(12) United States Patent
Zimmermann

(10) Patent No.: US 7,431,763 B2
(45) Date of Patent: *Oct. 7, 2008

(54) MAGNESIUM AMMONIUM PHOSPHATE CEMENT COMPOSITION

(75) Inventor: Michael Zimmermann, Frankfurt am Main (DE)

(73) Assignee: Kyphon SARL, Neuchatel (CH)

( * ) Notice: Subject to any disclaimer, the term of this patent is extended or adjusted under 35 U.S.C. 154(b) by 24 days.

This patent is subject to a terminal disclaimer.

(21) Appl. No.: 11/530,835

(22) Filed: Sep. 11, 2006

(65) Prior Publication Data

US 2007/0022912 A1    Feb. 1, 2007

Related U.S. Application Data

(63) Continuation of application No. 11/104,392, filed on Apr. 11, 2005, now Pat. No. 7,115,163, which is a continuation of application No. 10/772,857, filed on Feb. 4, 2004, now Pat. No. 6,908,506, which is a continuation of application No. 10/070,670, filed as application No. PCT/EP01/07605 on Jul. 3, 2001, now Pat. No. 6,692,563.

(30) Foreign Application Priority Data

Jul. 3, 2000    (DE) ............................... 100 32 220

(51) Int. Cl.
*C04B 9/11* (2006.01)
*A61L 24/02* (2006.01)

(52) U.S. Cl. ...................... 106/690; 106/691; 106/672; 106/674; 106/677; 106/680; 623/23.62

(58) Field of Classification Search ................. 106/690, 106/691, 35, 672, 674, 677, 680; 623/23.62
See application file for complete search history.

(56) References Cited

U.S. PATENT DOCUMENTS

| | | | |
|---|---|---|---|
| 4,518,430 A | 5/1985 | Brown et al. | |
| 4,612,053 A | 9/1986 | Brown et al. | |
| 4,959,104 A | 9/1990 | Iino et al. | |
| 5,149,368 A | 9/1992 | Liu et al. | |
| 5,262,166 A | 11/1993 | Liu et al. | |
| 5,281,265 A | 1/1994 | Liu | |
| 5,605,713 A | 2/1997 | Boltong | |
| 5,952,010 A | 9/1999 | Constantz | |
| 6,692,563 B2 | 2/2004 | Zimmermann | |
| 6,908,506 B2 | 6/2005 | Zimmermann | |

FOREIGN PATENT DOCUMENTS

| | | |
|---|---|---|
| EP | 0543765 A1 | 5/1993 |
| EP | 0835668 A1 | 4/1998 |
| WO | WO 95/13835 A1 | 5/1995 |
| WO | WO 96/14265 A1 | 5/1996 |

OTHER PUBLICATIONS

U.S. Appl. No. 11/104,392, filed Apr. 11, 2005, Zimmermann.
Brown et al., "A new calcium phosphate, water-setting cement" *Cement Research Progress* 1986 pp. 352-379 (1987).
Patent Abstract XP-002180738 (1 page total), Park et al., "Compositional effects of CaO-SiO2-P2O5 bioactive cement on hardening and hydroxyapatite formation" Yoop Hakhoechi, 31(5):502-512 (1994).
Patent Abstract XP-002180739 (1 page total), Nippon Electric Glass Co., "Bone-repair material for fast, strong bonding—contains glass and/or crystalline glass powder, a.q. phosphate solution and bond formation promoter" (1992).

*Primary Examiner*—C. Melissa Koslow
(74) *Attorney, Agent, or Firm*—Larson Newman Abel Polansky & White, LLP

(57) ABSTRACT

This invention relates to a cement, which comprises in its main phase of microcrystalline magnesium ammonium phosphate and nanoapatite after hardening and thus at the same time has considerable strength. The material is biologically degradable and is suitable for application in tooth cements, as bone replacement, as bone filler, as bone cement or as bone adhesive.

38 Claims, No Drawings

MAGNESIUM AMMONIUM PHOSPHATE CEMENT COMPOSITION

CROSS-REFERENCES TO RELATED APPLICATIONS

This application is a continuation of application Ser. No. 11/104,392, filed Apr. 11, 2005, now U.S. Pat. No. 7,115,163, which is a continuation of application Ser. No. 10/772,857, filed on Feb. 4, 2004, now U.S. Pat. No. 6,908,506 which is a continuation of application Ser. No. 10/070,670, filed on Mar. 4, 2002, now U.S. Pat. No. 6,692,563, which was a § 371 National Phase of PCT/EP01/07605, filed on Jul. 3, 2001, which claimed priority from DE 100 32 220.4, filed on Jul. 3, 2000, the full disclosures of which are incorporated herein by reference.

BACKGROUND OF THE INVENTION

Field of the Invention

The invention relates to a magnesium ammonium phosphate cement preparation, a process for its production and an associated use.

This invention relates in particular to a biologically degradable cement, which consists in its main phase of magnesium ammonium phosphates and nanoapatites after hardening and thus at the same time has a high strength.

The material may be used as bone replacement, for bone augmentation and for bone regeneration.

It may serve as excipient for pharmaceutical or biological active ingredients.

The most important mineral constituents in human bone and tooth enamel are calcium and phosphate. However, considerable quantities of sodium, magnesium and carbonate are also present.

It is known from precipitation studies of synthetic systems that sodium ions and carbonate ions may be incorporated very easily into calcium phosphate precipitates resulting in a molecular structure similar to apatite.

However, magnesium has a strong tendency to precipitate in a different structure not similar to apatite.

Calcium phosphate precipitated physiologically as bone and dentine is nanocrystalline. It cannot be seen from an X-ray diffractogram, due to line broadening, whether it is apatite or other structures.

Some scientists are of the opinion that so much magnesium occurs in bone and dentine that this cannot all be taken up in the apatite structure. Therefore, a mixed form of the mineral of nanoapatite and nanodolomite or nanostruvite is assumed here.

Calcium phosphates are not only biocompatible but are recognized by the living cell as belonging-to-the-body. Therefore, there are many biomaterials and medical products which consist partly of calcium phosphate.

Calcium phosphate ceramics have been on the market since about 1970, partly in the form of prefabricated blocks or as granules.

Implantations of these materials in bone structures are predominantly successful.

The biggest disadvantage of these systems is that the blocks have to be prefabricated and the granules drift away (flood out) from the side of the implantation. This often leads to failure of such implantations.

Calcium phosphate ceramics are most successful when they consist of hydroxyl-apatite (HA) or of beta-tertiary calcium phosphate ($\beta$-TCP, a whitlockite-like structure) or when the calcium phosphate ceramics consist of both, HA and $\beta$-TCP in variable ratios. HA is virtually non-resorbable from bone implantations, whereas $\beta$-TCP is slowly resorbed and replaced by new bone.

It is therefore possible to influence the degree of resorption of calcium phosphate ceramic by changing the $\beta$-TCP/HA ratio.

It is likewise possible to admix other resorbable materials, such as: monetite $CaHPO_4$, brushite $CaHPO_4\text{-}2H_2O$, calcite $CaCO_3$ and dolomite $CaMg(CO_3)_2$.

Since 1985 attempts have been made to develop calcium phosphate cements in order to avoid the disadvantages of prefabricated or granular-like calcium phosphate ceramics (W. E. Brown and L. C. Chow, "A new calcium phosphate, water-setting cement", Cem. Res. Prog. 1986 352-379 (1987)).

This includes a brushite cement not yet commercially available having a Ca/P molar ratio of the precipitated phase of 1.00. This phase is not nanocrystalline but microcrystalline.

All the other calcium phosphate cements developed hitherto have a nanocrystalline precipitation structure and a Ca/P molar ratio of $>=1.5$, which may be further increased by addition of carbonate. These materials are known under U.S. Pat. No. 5,605,713; European application 0 835 668; World 96/14265, and some of these materials are already on the market.

There are contradictory reports regarding the resorbability of these materials after implantations in bone and soft tissue.

In each case, calcium phosphate cements based on hydroxylapatite (HA) which are not resorbable (HA ceramics see above) and calcium phosphate cements based on deficient calcium hydroxylapatites (CDHA, calcium deficient hydroxylapatites) which are good osteotransductively, are differentiated.

This means for the last-mentioned case, that they may be resorbed by osteoclasts and may be replaced by new bone tissue from osteoblasts.

Resorption of these cements depends crucially on the local bone transformation mechanisms.

Today, most surgeons require a calcium phosphate cement, in which initially a mechanically supporting mode of action is brought to bear, but the final resorption lags behind independently of the local transformation mechanisms of the bone, that is that the material is completely degraded. In addition, it is known in orthopaedics that vital bone only remains where it is required from the biomechanical point of view. This is known as the so-called Wolff's Law. Consequently, if a calcium phosphate cement introduced into a bone defect has a higher compressive strength than the bone surrounding it and this high compressive strength remains unchanged, this leads to degradation of bone tissue lying around the implant (here calcium phosphate cement).

In order to fulfill this requirement, even if only partly, some manufacturers have admixed substances into their CDHA cements which are similar to nanoapatite, which are passively resorbed by the bodily fluids due to the concentration gradients, such as for example monetite ($CaHPO_4$) or calcite ($CaCO_3$) as known from European 0 543 765.

However, this only partly solves the problem. A cement is also required which can be resorbed completely passively and in which the resorption front and the deposition front are in direct contact.

Gypsum for example does not fulfill this requirement. Gypsum is resorbed so rapidly that there is always a gaping hole between the resorption front and the deposition front and these materials do not have adequate supporting function due to their low resistance to pressure. Such materials are disclosed, for example under U.S. Pat. No. 5,281,265.

For these reasons, it is desirable to provide a bone replacement material, which initially takes over the lost supporting function of the bone with high resistance to pressure, but then successively decreases in resistance to pressure, as a result of which the endogenous bone transformation processes (remodeling) are stimulated and hence more rapid osteoneogenesis and hence also active resorption of the bone replacement material is introduced. This may also be achieved by incorporating a slightly soluble substance, for example into a hardening cement paste. Because bone grows well into macroporous structures, it is advantageous to admix granular or pellet-like, solubilizing substances consisting of, for example sugars, salts (for example NaCl) or gypsum ($CaSO_4$) into the cement paste. They are then leached out very rapidly in the body from the hardened cement structure and a porous sponge-like structure remains. Production of a porous (finished) cement outside the body is also conceivable.

In order to be able to use a cement for dental applications, such as for example filling and sealing of small dentine channels, filling of tooth cavities after vital extirpation, utilizing such a cement as sub-filling material in endodontology, such a material may not shrink to prevent passage of bacteria. Even a material having low-grade expandable properties would be desirable.

It is the object of the invention to provide a cement preparation, with which the disadvantages of the state of the art are avoided.

BRIEF SUMMARY OF THE INVENTION

The present invention provides a magnesium ammonium phosphate cement preparation, comprising: a powder mixture having molar quantities of the components calcium (Ca), magnesium (Mg) and orthophosphate (P) in the mixture in the ranges $1.00 < Ca/P < 1.50$ and $0 < Mg/P < 0.50$; an ammonium salt; and water and/or an aqueous solution.

In one embodiment, the present invention provides a magnesium ammonium phosphate cement preparation, comprising: a powder mixture, consisting of ($\alpha$-TCP, $\beta$-TCP, $MgHPO_4 \times 3H_2O$, $KH_2PO_4$ and $Na_2HPO_4$; an ammonium salt; and water and/or an aqueous solution.

In another embodiment, the present invention provides a magnesium ammonium phosphate cement preparation, comprising: a powder mixture consisting of: $\alpha/\beta$-TCP, $MgHPO_4 \times 3H_2O$, $KH_2PO_4$, $Na_2HPO_4$ and $Mg_3(PO_4)_2$; and an aqueous solution containing ammonium ions.

In a further embodiment, the present invention provides a magnesium ammonium phosphate cement preparation, comprising: a powder mixture consisting of: $\alpha/\beta$-TCP, $MgHPO_4 \times 3H_2O$, $KH_2PO_4$, $Na_2HPO_4$ and $Mg_3(PO_4)_2$; and an aqueous solution containing ammonium ions.

In yet another embodiment, the present invention provides a magnesium ammonium phosphate cement preparation, comprising: a powder mixture consisting of: $\alpha/\beta$-TCP, $MgHPO_4 \times 3H_2O$, $KH_2PO_4$, $Na_2HPO_4$ and $Mg_3(PO_4)_2$; and an aqueous solution containing ammonium ions.

The preparations of the present invention can also include one or more of the following features:
- the aqueous solution is an aqueous solution of an ammonium salt having a pH value in the range from $7 < pH < 12$;
- the ammonium salt is present in the powder mixture and the molar quantities of the components calcium (Ca), magnesium (Mg), orthophosphate (P) and ammonium ($NH_4$) lie in the ranges $1.00 < Ca/P < 1.50$ and $0 < Mg/P < 0.50$ and $0 < NH_4 < 0.50$;
- the powder mixture comprises $\alpha/\beta$-tertiary calcium phosphate ($\alpha/\beta$—TCP) and preferably $MgHPO_4 \times 3H_2O$;
- the powder mixture, apart from $\alpha/\beta$-TCP and $MgHPO_4 \times 3H_2O$, additionally contains $Mg_3(PO_4)_2$;
- the aqueous solution comprises an aqueous $(NH_4)_2SO_4$ solution;
- the powder mixture comprises $(NH_4)_2SO_4$;
- a mixing liquid consists of an aqueous $(NH_4)_2HPO_4$ solution;
- the powder mixture additionally comprises $KH_2PO_4$;
- the powder mixture additionally comprises $Na_2HPO_4$;
- additionally $SrCO_3$;
- the level of $SrCO_3$ is 0.01 to 10 wt. %, preferably 0.1 to 5 wt. %, based on the total weight of the preparation;
- an aqueous solution of an ammonium salt as mixing liquid;
- an aqueous solution of a magnesium salt as mixing liquid;
- an aqueous solution of a strontium salt as mixing liquid;
- as additional component, ZnO in the powder mixture and/or in the mixing liquid;
- the powder mixture additionally contains $Ca_2NaK(PO_4)_2$ and/or $CaKPO_4$;
- as an additional component, fluoride ions in the powder mixture and/or in the mixing liquid; and
- as additional components, pharmaceutical and/or bioactive active ingredients in the powder mixture and/or in the mixing liquid, preferably antibiotics, cytostatic agents, analgesics, disinfectants, growth factors, proteins or elastin inhibitors in therapeutic doses.

The invention also provides a process for producing a magnesium ammonium phosphate cement wherein the powder mixture is mixed with the mixing liquid while achieving uniform distribution of the liquid in the powder mixture and the paste thus obtained is applied on or to the target zone or is introduced into the target zone and is allowed to harden, wherein the components react such that the cement formed has microcrystalline magnesium ammonium phosphate.

In another embodiment, the invention provides a process for producing a magnesium ammonium phosphate cement using a magnesium ammonium cement preparation, in which the powder mixture is mixed with the mixing liquid while achieving uniform distribution of the liquid in the powder mixture and the paste thus obtained is applied on or to the target zone or is introduced into the target zone and is allowed to harden with formation of cement containing microcrystalline magnesium ammonium phosphate.

The process in accord with the present invention also can include one or more of the following features:
- granular, thus granular particles which are slightly soluble in aqueous liquids, between about 10 μm and about 300 μm, preferably between 50 μm and 200 μm, are added to the powder mixture; and
- the granular particles preferably consist of NaCl, sugars, $CaSO_4$, $\beta$-TCP, polylactides, polyglycolides or polylactide/polyglycolide copolymer, $CaCO_3$, $CaHPO_4$.

The preparations of the present invention can be used, e.g., for medical purposes, for tooth cement and for bone replacement or bone filler or bone cement or bone adhesive.

DETAILED DESCRIPTION OF THE INVENTION

The problems in the state of the art are preferably solved by the present invention to the effect that it is possible to set the ability for expansion of the hardening cement paste by variation in the admixture of strontium salts. In tests, as shown in the examples, it is namely shown that the ability for expansion of the cement mixture, the main phase of which is the magnesium ammonium phosphate in the hardened state, decreases with increasing weight portion of strontium salts in the total powder mixture. Consequently, with this invention a material for endodontology may be provided, which also has an expandable property in addition to adequate mechanically loadable stability.

An object of this invention is to provide a material for bone replacement, for bone augmentation and bone regeneration, which may be resorbed in a limited time and the resistance to pressure of which may decrease adapted to the regeneration requirements of the body.

Another object of the invention to provide a material that may be created, prepared and modeled under normal temperature conditions, preferably body temperature, in other words a cement.

It is characteristic of the material provided, that it may additionally be adjusted by the intensity of the degree of sintering of the $Mg_3(PO_4)_2$ introduced in its processing time, in particular at room temperature, wherein the rate of solubility on the surface of these particles is controlled by the degree of sintering and the density of the $Mg_3(PO_4)_2$ used resulting therefrom, so that the precipitation of the Ca/Mg/phosphate compound settling out necessary for solidification may be controlled.

Furthermore, it is the object of this invention to provide a phosphate cement having partial solubility, preferably due to the slow solubility of the magnesium ammonium phosphate apatite structure (cement).

Furthermore, it is the object of the present invention to describe a reaction process, which leads to the formation of a magnesium ammonium phosphate cement from a number of individual components and which hardens in a clinically acceptable time at room and/or body temperature.

Furthermore, it is the object of the present invention to provide a material which becomes adequately hard and stable in a clinically acceptable time and which has a strong ability for adhesion to mineralized surfaces.

Furthermore, the object of the invention is the material disclosed according to the invention which is characterized by a strong ability for adhesion to metallic surfaces.

Furthermore, it is the object of the present invention to provide a resorbable cement, which can be injected in the form of a mixed paste.

One aspect of this invention is that the end product consists of a powder mixture having a molar Ca/P ratio in the range from 1.00 to 1.50. (P represents orthophosphate).

In addition, it is essential that the molar ratio Mg/P ratio of this powder mixture includes the range from 0 to 1.00.

In order to mix and to shape a cement paste, which hardens within an acceptable time, these powder mixtures must be adequately reactive. In order to achieve this, a further aspect of this invention is to mix the powder mixtures with suitable quantities of slightly basic (7<pH<12), aqueous solutions of soluble ionic constituents, such as for example: $Na_3PO_4$, $K_2CO_3$ and/or $Na_2CO_3$ in combination with $(NH_4)_2HPO_4$.

A further feature of this invention is that granular but granular solids which are thus slightly soluble in the bodily fluid are admixed to the hardening cement paste, so that after settling-out thereof, a microporous to macroporous pore system results.

A further aspect of this invention is that these cements reach their maximum solidity within a few hours.

A further feature of this invention lies in the ability for expansion of the cement during setting. The expansivity is determined or adjusted by the relative proportion of an admixed strontium salt.

A further feature of this invention is that the hardened cement consists of microcrystalline magnesium ammonium phosphate.

A further feature of this invention is that the initial hardening time of the cement may be set at 1 to 40 minutes and the final hardening time at 2.5 to 60 minutes. (according to ASTM C266-89)

A further feature of this invention is that the cement may reach a maximum compressive strength of over 50 MPa.

A further feature of this invention is that the cement paste can be injected before reaching the initial hardening time.

A further feature of this invention is that the cement paste may serve as excipient for other materials which are not Ca, Mg and/or phosphate. For example ZnO, pharmaceutical active ingredients (antibiotics, cytostatic agents, growth factors) or other bioactive substances.

Further features and advantages of the invention can be seen from the description of exemplary embodiments.

EXAMPLES

The following symbols are used in the examples:
P=powder mixture
L=liquid
UP=liquid/powder ratio in ml/g
$t_i$=initial hardening time (according to ASTM standard C266-89, Gilmoore needle)
$t_F$=final (end) hardening time (according to ASTM standard C266-89, Gilmoore needle)
D(x h)=compressive strength in Mpa after x hours storage in 0.9% strength NaCl solution at 37° C.
Production: After weighing out all constituents, the powder mixture is homogenized in a ball mill for about 20 minutes.

Example 1

| | | | |
|---|---|---|---|
| P = | 60 g α-$Ca_3(PO_4)_2$ + 6 g $MgHPO_4$•$3H_2O$ + 5 g $MgSO_4$•$7H_2O$ | | |
| L = | 2M $(NH_4)_2HPO_4$ | L/P = | 0.40 |
| $t_i$ = | 9 | $T_F$ = | 21 |
| D(18) | 18.4 ± 1.5 | | |
| D(72) | 26.1 ± 4.0 | | |

Example 2

| | | | |
|---|---|---|---|
| P = | 60 g α-$Ca_3(PO_4)_2$ + 14 g $MgHPO_4$•$3H_2O$ + 2 g $Mg(OH)_2$ | | |
| L = | 3.5 M $(NH_4)_2HPO_4$ | L/P = | 0.35 |
| $t_i$ = | 3 | $T_F$ = | 7 |
| D(18) | 32.5 ± 3.5 | | |
| D(72) | 46.9 ± 5.4 | | |

Example 3

| | | | |
|---|---|---|---|
| P = | 60 g α-$Ca_3(PO_4)_2$ + 16 g $MgHPO_4$•$3H_2O$ + 3 g $Na(PO_4)_3$•$12H_2O$ | | |
| L = | 3.5 M $(NH_4)_2HPO_4$ | L/P = | 0.35 |
| $t_i$ = | 6 | $T_F$ = | 14 |
| D(18) | 44.7 ± 3.4 | | |
| D(72) | 51.7 ± 5.0 | | |

Example 4

| | |
|---|---|
| P = | 60 g α-Ca$_3$(PO$_4$)$_2$ + 14 g MgHPO$_4$•3H$_2$O + 2 g ZnO |
| L = | 3.5 M (NH$_4$)$_2$HPO$_4$   L/P = 0.35 |
| t$_i$ = | 6   T$_F$ = 23 |
| D(18) | 35.1 ± 5.3 |
| D(72) | 42.9 ± 0.8 |

Example 5

| | |
|---|---|
| P = | 45 g CaHPO$_4$•2H$_2$O + 14 g MgHPO$_4$•3H$_2$O + 6 g Mg(OH)$_2$ |
| L = | 2 M (NH$_4$)$_2$HPO$_4$   L/P = 0.40 |
| t$_i$ = | 2.5   T$_F$ = 7.5 |
| D(18) | 3.8 ± 1.2 |

Example 6

| | |
|---|---|
| P = | 45 g CaHPO$_4$•2H$_2$O + 14 g CaCO$_3$ + 14 g MgHPO$_4$•3H$_2$O + 6 g ZnO |
| L = | 3.5 M (NH$_4$)$_2$HPO$_4$   L/P = 0.35 |
| t$_i$ = | 2   T$_F$ = 4 |
| D(18) | 3.8 ± 1.2 |

Example 7

| | |
|---|---|
| P = | 60 g α-Ca$_3$(PO$_4$)$_2$ + 16 g MgHPO$_4$•3H$_2$O + 5 g β-Ca$_3$(PO$_4$)$_2$ |
| L = | 3.5 M (NH$_4$)$_2$HPO$_4$   L/P = 0.35 |
| t$_i$ = | 4   T$_F$ = 9 |
| D(2) | 59.3 ± 1.0 |
| D(4) | 55.6 ± 5.0 |
| D(18) | 61.6 ± 5.0 |
| D(72) | 51.5 ± 6.6 |
| D(18d) | 28.1 ± 4.6 |

Example 8

| | |
|---|---|
| P = | 60 g α-Ca$_3$(PO$_4$)$_2$ + 16 g MgHPO$_4$•3H$_2$O + 5 g β-Ca$_3$(PO$_4$)$_2$ |
| L = | 3.5 M (NH$_4$)$_2$HPO$_4$   L/P = 0.35 |
| t$_i$ = | 3.5   T$_F$ = 11.5 |
| D(2) | 54.4 ± 3.3 |
| D(18) | 65.6 ± 5.3 |
| D(4d) | 56.6 ± 8.6 |
| D(18d) | 36.3 ± 2.4 |
| D(30d) | 30.0 ± 3.0 |

Example 9

| | |
|---|---|
| P = | 60 g α-Ca$_3$(PO$_4$)$_2$ + 16 g MgHPO$_4$•3H$_2$O + 5 g β-Ca$_3$(PO$_4$)$_2$ + 0.8 g SrCO$_3$ |
| L = | 3.5 M (NH$_4$)$_2$HPO$_4$   L/P = 0.35 |
| t$_i$ = | 5.5   T$_F$ = 13 |
| D(2.5) | 54.3 ± 4.6 |
| D(5) | 61.1 ± 5.5 |
| D(18) | 70.1 ± 5.7 |
| D(4d) | 74.3 ± 9.3 |
| D(18d) | 43.4 ± 3.4 |
| D(30d) | 34.0 ± 4.0 |

Example 10

| | |
|---|---|
| P = | 60 g α-Ca$_3$(PO$_4$)$_2$ + 8 g MgHPO$_4$•3H$_2$O + 2 g (NH$_4$)$_2$SO$_4$ + 2 g KH$_2$PO$_4$ + 3.5 g SrCO$_3$ |
| L = | 3.5 M (NH$_4$)$_2$HPO$_4$   L/P = 0.30 |
| t$_i$ = |    T$_F$ = |
| D(0.25) | 11.2 ± 0.8 |
| D(0.5) | 17.2 ± 1.8 |
| D(2) | 31.7 ± 1.3 |
| D(6) | 39.7 ± 0.63 |
| D(3d) | 56.5 ± 4.9 |

Example 11

| | |
|---|---|
| P = | 60 g α-Ca$_3$(PO$_4$)$_2$ + 8 g MgHPO$_4$•3H$_2$O + 4 g (NH$_4$)H$_2$PO$_4$ + 1 g SrCO$_3$ |
| L = | 3.5 M (NH$_4$)$_2$HPO$_4$   L/P = 0.37 |
| t$_i$ = |    T$_F$ = |
| D(2) | 22.6 ± 1.0 |
| D(6) | 31.4 ± 1.1 |
| D(18) | 45.8 ± 1.8 |
| D(3d) | 45.7 ± 2.9 |
| D(35d) | 11.5 ± 1.2 |

Example 12

| | |
|---|---|
| P = | 60 g α-Ca$_3$(PO$_4$)$_2$ + 17.4 g MgHPO$_4$•3H$_2$O + 7 g (NH$_4$)$_2$SO$_4$ + 1.7 g SrCO$_3$ |
| L = | 3.5 M (NH$_4$)$_2$HPO$_4$   L/P = 0.35 |
| t$_i$ = |    T$_F$ = |
| D(2) | 43.3 ± 2.9 |
| D(6) | 45.4 ± 4.4 |
| D(18) | 45.8 ± 1.8 |
| D(3d) | 45.7 ± 2.9 |
| D(28d) | 19.5 ± 5.1 |

Example 13

| | |
|---|---|
| P = | 60 g α-Ca$_3$(PO$_4$)$_2$ + 20 g CaHPO$_4$ + 8 g CaCO$_3$ + 1 g MgHPO$_4$ + 1.7 g SrCO$_3$ |
| L = | 3.5 M (NH$_4$)$_2$HPO$_4$   L/P = 0.35 |
| t$_i$ = | 2.5   T$_F$ = 8 |
| D(2) | 43.3 ± 2.9 |
| D(6) | 49.4 ± 3.7 |
| D(18) | 54.3 ± 2.5 |

-continued

| D(3d)  | 53.6 ± 3.1 |
| D(28d) | 54.5 ± 1.9 |

Example 14

| P = | 60 g β-Ca$_3$(PO$_4$)$_2$ + 17.4 g MgHPO$_4$·3H$_2$O + 1.7 g SrCO$_3$ | | |
| L = | 3.5 M (NH$_4$)$_2$HPO$_4$ | L/P = | 0.35 |
| t$_i$ = | 3.5 | T$_F$ = | 9 |

Example 15

| P = | 60 g α-TCP + 34.8 g MgHPO$_4$ × 3H$_2$O + 13.2 g (NH$_4$)SO$_4$ | | |
| L = | 5% NaHCO$_3$ | L/P = | 0.35 |
| t$_i$ = | 3 | T$_F$ = | 10 |

Example 16

| P = | 60 g α-TCP + 16 g MgHPO$_4$ × 3H$_2$O + 5 g β-TCP + 20 g NaCL (diameter 150 µm) | | |
| L = | 3.5 M (NH$_4$)$_2$HPO$_4$ | L/P = | 0.35 |
| t$_i$ = | 5 | T$_F$ = | 12 |

Example 17

P=60 g α-TCP+6 g Mg$_3$(PO$_4$)$_2$+10 g KH$_2$PO$_4$+5 g β3-TCP
Mixing solution: 3.2 molar solution (NH$_4$)$_2$HPO$_4$
L/P=0.35
T$_i$=10.8 t$_f$=20
D(2)–18.5±1.0
D(18)=48.3±1.8

While the above is a complete description of the preferred embodiments of the invention, various alternatives, modifications, and equivalents may be used. Therefore, the above description should not be taken as limiting the scope of the invention which is defined by the appended claims.

What is claimed is:

1. A magnesium ammonium phosphate cement preparation comprising:
   a) a powder mixture comprising a calcium (Ca) orthophosphate and magnesium (Mg) orthophosphate, wherein the molar quantities of Mg and orthophosphate are in the range Mg/orthophosphate (P)<1.0; and molar quantities of Ca and orthophosphate are in the range Ca/orthophosphate (P)<1.5; and
   b) an ammonium salt.

2. The preparation of claim 1, further comprising a strontium salt.

3. The preparation according to claim 2, wherein the strontium salt is SrCO$_3$.

4. The preparation according to claim 2, wherein the strontium salt is present in the range of 0.01 to 10 wt. %, based on the total weight of the preparation.

5. The preparation of claim 1, further comprising an aqueous solution.

6. The preparation of claim 5, wherein the preparation has a final hardening time of 2.5 to 60 minutes (measured according to ASTM C266-89).

7. The preparation of claim 5, wherein the ammonium salt comprises an aqueous solution having a pH in the range from 7 to 12.

8. The preparation according to claim 5, wherein the aqueous solution comprises fluoride ions in the mixing liquid.

9. The preparation of claim 2, further comprising an aqueous solution.

10. The preparation according to claim 9, wherein the aqueous solution comprises the ammonium salt or the strontium salt in the form of a mixing liquid.

11. The preparation according to claim 1, wherein the ammonium salt is present in the powder mixture at molar quantity of ammonium (NH$_4$) less than 0.5.

12. The preparation according to claim 2, wherein the ammonium salt is present in the powder mixture and the molar quantities of the components calcium (Ca) orthophosphate, magnesium (Mg) orthophosphate, and ammonium (NH$_4$) are in the range Ca/orthophosphate (P)<1.50 and 0<Mg/orthophosphate (P)<1.0 and 0<NH$_4$<0.50.

13. The preparation according to claim 1, further comprising Mg$_3$(PO$_4$)$_2$.

14. The preparation according to claim 13, further comprising wherein the Mg$_3$(PO$_4$)$_2$ is sintered.

15. The preparation according to claim 1, further comprising ZnO.

16. The preparation according to claim 1, further comprising fluoride ions.

17. The preparation according to claim 1, further comprising granular particles.

18. The preparation according to claim 17, wherein the granular particles are slightly soluble in aqueous liquids.

19. The preparation according to claim 17, wherein the granular particles have a diameter of between 10 µm and 300 µm.

20. The preparation according to claim 17, wherein the granular particles are a substance selected from the group consisting of NaCl, sugars, CaSO$_4$, β-TCP, polylactides, polyglycolides or polylactide/polyglycolide copolymer, CaCO$_3$ and CaHPO$_4$.

21. The preparation according to claim 1, wherein the preparation further comprises a pharmaceutical and/or a bioactive active ingredient.

22. The preparation according to claim 21, wherein the pharmaceutical and/or bioactive active ingredient comprises a therapeutic dose of a component selected from the group consisting of antibiotics, cytostatic agents, analgesics, disinfectants, growth factors, proteins or elastin inhibitors.

23. The preparation of claim 1, wherein the calcium orthophosphate α-TCP.

24. The preparation of claim 1, comprising a magnesium hydrogen orthophosphate.

25. A magnesium ammonium phosphate cement preparation comprising:
   a) an ammonium salt; and
   b) a powder mixture comprising the components calcium (Ca) orthophosphate (P), magnesium (Mg), orthophosphate, and granular particles, wherein the molar quantities of the components Mg and orthophosphate are in the range Mg/orthophosphate (P)<1.0 and molar quantities of Ca and orthophosphate are in the range Ca/orthophosphate (P)<1.5, wherein the granular particles are configured to leach from a hardened cement structure formed from the cement preparation, leaving the hardened cement structure porous.

26. The preparation according to claim 25, wherein the granular particles are slightly soluble in aqueous liquids.

27. The preparation according to claim 25, wherein the granular particles have a diameter of between 10 µm and 300 µm.

28. The preparation according to claim 25, wherein the granular particles are a substance selected from the group consisting of NaCl, sugars, $CaSO_4$, β-TCP, polylactides, polyglycolides or polylactide/polyglycolide copolymer, $CaCO_3$ and $CaHPO_4$.

29. The preparation according to claim 25, further comprising a strontium salt.

30. The preparation according to claim 25, further comprising an aqueous solution.

31. A magnesium ammonium phosphate cement preparation comprising:
   a) an ammonium salt and/or strontium salt; and
   b) a powder mixture comprising calcium (Ca) orthophosphate (P) and magnesium (Mg) orthophosphate, wherein the molar quantities of Ca and orthophosphate are in the range Ca/orthophosphate (P)<1.5 and the molar quantities of the components Mg and orthophosphate are in the range Mg/orthophosphate (P)<1.0, wherein the cement preparation when hardened forms a bone replacement material that stimulates endogenous bone transformation processes and allows for active resorption of the bone replacement material.

32. The preparation according to claim 31, further comprising granular particles.

33. The preparation according to claim 32, wherein the granular particles are slightly soluble in aqueous liquids.

34. The preparation according to claim 32, wherein the granular particles have a diameter of between 10 µm and 300 µm.

35. The preparation according to claim 32, wherein the granular particles are a substance selected from the group consisting of NaCl, sugars, $CaSO_4$, β-TCP, polylactides, polyglycolides or polylactide/polyglycolide copolymer, $CaCO_3$ and $CaHPO_4$.

36. The preparation according to claim 31, wherein the strontium salt is $SrCO_3$.

37. The preparation according to claim 31, wherein the strontium salt is present in the range of 0.01 to 10 wt. %, based on the total weight of the preparation.

38. The preparation of claim 31, further comprising an aqueous solution.

\* \* \* \* \*